United States Patent [19]

Berg

[11] Patent Number: 4,904,346

[45] Date of Patent: * Feb. 27, 1990

[54] SEPARATION OF M-DIISOPROPYL BENZENE FROM P-DIISOPROPYL BENZENE BY EXTRACTIVE DISTILLATION

[75] Inventor: Lloyd Berg, 1314 S. Third Ave., Bozeman, Mont. 59715

[73] Assignee: Lloyd Berg

[*] Notice: The portion of the term of this patent subsequent to Aug. 8, 2006 has been disclaimed.

[21] Appl. No.: 407,861

[22] Filed: Sep. 15, 1989

[51] Int. Cl.$^4$ ............................ B01D 3/40; C07C 7/08
[52] U.S. Cl. ........................................ 203/60; 203/63; 203/64; 585/808; 585/866
[58] Field of Search ............................ 203/60, 63, 64; 585/804, 808, 807, 866

[56] References Cited

U.S. PATENT DOCUMENTS

| | | | |
|---|---|---|---|
| 2,461,993 | 2/1949 | Mckinnis | 203/62 |
| 2,805,258 | 9/1957 | Boodman et al. | 585/839 |
| 2,840,621 | 6/1958 | Corson et al. | 585/839 |
| 3,222,349 | 12/1965 | Holder | 585/804 |

FOREIGN PATENT DOCUMENTS

| | | | |
|---|---|---|---|
| 49-47326 | 5/1975 | Japan | 585/866 |
| 50-70324 | 6/1975 | Japan | 585/864 |

*Primary Examiner*—Wilbur Bascomb

[57] ABSTRACT

Meta and para-diisopropyl benzenes cannot be easily separated from each other by distillation because of the closeness of their vapor pressures. m-Diisopropyl benzene can be readily removed from p-diisopropyl benzene by extractive distillation using certain high boiling organic compounds. Effective extractive agents are diphenyl ether, dimethyl adipate, diisononyl adipate, tributyl phosphate and ethylene glycol phenyl ether.

5 Claims, No Drawings

SEPARATION OF M-DIISOPROPYL BENZENE FROM P-DIISOPROPYL BENZENE BY EXTRACTIVE DISTILLATION

FIELD OF THE INVENTION

This invention relates to a method for separating m-diisopropyl benzene from p-diisopropyl benzene using certain high boiling organic compounds in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in the rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

In the manufacture of cumene, also called isipropyl benzene, by the alkylation of benzene with propylene, the most prevalent by-products are the diisopropyl benzenes with the meta and para isomers comprising most of the by-product. m-Diisopropyl benzene (m-DIPB) boils at 203.2° C., p-diisopropyl benzene (p-DIPB) boils at 210.3° C. and these two have a relative volatility of 1.14. The difficulty of separating these two by rectification can be shown by the data in Table 1.

TABLE 1

| Plates Required To Effect Separation in 99% Purity | | |
|---|---|---|
| Relative Volatility | Theoretical Plates | Actual Plates, 75% Efficiency |
| 1.14 | 71 | 95 |
| 1.19 | 53 | 71 |
| 1.21 | 48 | 64 |
| 1.25 | 41 | 55 |
| 1.26 | 40 | 54 |

Table 1 shows that rectification of m-DIPB from p-DIPB in 99% purity requires 95 actual plates. Using extractive distillation with an agent yielding a relative volatility of 1.26 would require only 54 actual plates.

Thus extractive distillation would be an attractive method of effecting the separation of these isomers if agents can be found that (1) will increase the relative volatility of m-DIPB to p-DIPB and (2) are easy to recover from the p-DIPB.

Extractive distillation typically requires the addition of an equal amount or twice as much extractive agent as the formic acid-dioxane on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The objective of this invention is to provide a process or method of extractive distillation that will enhance the relative volatility of m-DIPB from p-DIPB in their separation in a rectification column. It is a further object of this invention to identify organic compounds which in addition to the above constraints, are stable, can be separated from m-DIPB by solvent extraction and can be recycled to the extractive distillation and reused with little decomposition.

SUMMARY OF THE INVENTION

The objects of this invention are provided by a process for separating m-DIPB from p-DIPB which entails the use of certain high boiling organic compounds in an extractive distillation process.

DETAILED DESCRIPTION OF THE INVENTION

I have discovered that certain high boiling organic compounds will effectively enhance the relative volatility of m-DIPB from p-DIPB and permit the separation of m-DIPB from p-DIPB by rectification when employed as the agent in extractive distillation.

TABLE 2

| Effective Extractive Distillation Agents | | |
|---|---|---|
| Compounds | p-DIPB - Agent B.P. °C. @ 23" Vac. | Relative Volatility |
| Diphenyl ether | 106 | 1.26 |
| Dimethyl adipate | 104 | 1.26 |
| Diisononyl adipate | 102 | 1.25 |
| Tributyl phosphate | 106 | 1.21 |
| Ethylene glycol phenyl ether | 110 | 1.19 |

TABLE 3

| Some Ineffective Agents Investigated | |
|---|---|
| Compounds | Relative Volatility |
| Sulfolane | 1.16 |

TABLE 3-continued
Some Ineffective Agents Investigated

| Compounds | Relative Volatility |
| --- | --- |
| Dipropylene glycol dibenzoate | 1.08 |
| Benzyl benzoate | 1.14 |
| Glycerol triacetate | 1.13 |
| Diethylene glycol butyl ether acetate | 1.03 |
| Triethylene glycol diacetate | 1.17 |
| 2-Nitrotoluene | 1.14 |
| 4-Nitrotoluene | 1.10 |
| Dibenzyl ether | 1.16 |
| Dimethyl phthalate | 1.05 |
| Diethylene glycol dibutyl ether | 1.14 |
| Ethyl phenyl acetate | 1.17 |
| Dimethyl sebacate | 1.03 |
| Triisononyl mellitate | 1.15 |
| Pelargonic acid | 1.15 |
| 2,2-Dimethyl octanoic acid | 1.07 |
| n-Decanoic acid | 1.09 |
| Diethylene glycol hexyl ether | 1.10 |
| Hexyl ether | 1.14 |

Table 2 lists the compounds that I have found to be effective. Table 3 lists some compounds found to be ineffective. The data in Tables 2 and 3 was obtained in a vapor-liquid equilibrium still. In each case, the starting material was a mixture containing 50 extractive agent, 25% m-DIPB and 25% p-DIPB. The boiling point is listed for each mixture at 23 inches of vacuum. The relative volatilities shown were obtained at that reduced pressure.

The agents which are effective are diphenyl ether, dimethyl adipate, diisononyl adipate, tributyl phosphate and ethylene glycol phenyl ether. The data in Table 2 indicates that, for example, one part of diphenyl ether mixed with one part of m-DIPB-p-DIPB mixture gives a relative volatility of 1.26.

THE USEFULNESS OF THE INVENTION

The usefulness or utility of this invention can be demonstrated by referring to the data shown in Tables 1, 2 and 3. All of the successful extractive distillation agents show that m-DIPB can be separated from p-DIPB by means of extractive distillation in a rectification column and that the ease of separation as measured by relative volatility is considerable. Without these extractive distillation agents only a slight improvement will occur in a rectification column.

WORKING EXAMPLES

Example 1

Thirty-five grams of m-DIPB, 25 grams of p-DIPB and 50 grams of diphenyl ether were charged to an Othmer type vapor-liquid equilibrium still and refluxed for five hours. Analysis by gas chromatography gave a vapor composition of 65.9% m-DIPB, 34.1% p-DIPB; a liquid composition of 60.5% m-DIPB, 39.5% p-DIPB. This indicates a relative volatility of m-DIPB to p-DIPB of 1.26.

Example 2

Fifty grams of the m-DIPB-p-DIPB mixture and 50 grams of diisononyl adipate were charged to the vapor liquid equilibrium still and refluxed for three hours. Analysis indicated a vapor composition of 63.6% m-DIPB, 36.4% p-DIPB; a liquid ccomposition of 58.3% m-DIPB, 41.7% p-DIPB which is a relative volatility of 1.25. Both Examples 1 and 2 were run at 23 inches of vacuum to lower the boiling points.

Example 3

A glass perforated plate rectification column was calibrated with ethylbenzene and p-xylene which possesses a relative volatility of 1.06 and found to have 5.3 theoretical plates. A solution comprising 100 grams of m-DIPB and 100 grams of p-DIPB was placed in the stillpot and heated under 23 inches of vacuum. When refluxing began, an extractive agent comprising diphenyl ether was pumped into the column at a rate of 20 ml/min. The temperature of tye extractive agent as it entered the column was 85° C. After establishing the feed rate of the extractive agent, the heat input to the m-DIPB and p-DIPB in the stillpot was adjusted to give a total reflux rate of 10–20 ml/min. After one hour of operation, the overhead and bottoms samples of approximately two ml. were collected and analysed by gas chromatography. The overhead analysis was 23.9% m-DIPB, 76.1% p-DIPB. The bottoms analysis was 8.6% m-DIPB, 91.4% p-DIPB. Using these compositions in the Fenske equation, with the number of theoretical plates in the column being 5.4, gave an average relative volatility of 1.254 for each theoretical plate.

I claim:

1. A method for recovering m-diisopropylbenzene (m-DIPB) from a mixture of m-DIPB and p-diisopropylbenzene (p-DIPB) which comprises distilling a mixture of m-DIPB and p-DIPB in a rectification column in the presence of an extractive agent, recovering the m-DIPB as overhead product and obtaining the p-DIPB and the extractive agent from the stillpot, wherein said extractive agent comprises diphenyl ether.

2. A method for recovering m-diisopropylbenzene (m-DIPB) from a mixture of m-DIPB and p-diisopropylbenzene (p-DIPB) which comprises distilling a mixture of m-DIPB and p-DIPB in a rectification column in the presence of an extractive agent, recovering the m-DIPB as overhead product and obtaining the p-DIPB and the extractive agent from the stillpot, wherein said extractive agent comprises ethylene glycol phenyl ether.

3. A method for recovering m-diisopropylbenzene (m-DIPB) from a mixture of m-DIPB and p-diisopropylbenzene (p-DIPB) which comprises distilling a mixture of m-DIPB and p-DIPB in a rectification column in the presence of an extractive agent, recovering the m-DIPB as overhead product and obtaining the p-DIPB and the extractive agent from the stillpot, wherein said extractive agent comprises dimethyl adipate.

4. A method for recovering m-diisopropylbenzene (m-DIPB) from a mixture of m-DIPB and p-diisopropylbenzene (p-DIPB) which comprises distilling a mixture of m-DIPB and p-DIPB in a rectification column in the presence of an extractive agent, recovering the m-DIPB as overhead product and obtaining the p-DIPB and the extractive agent from the stillpot, wherein said extractive agent comprises diisononyl adipate.

5. A method for recovering m-diisopropylbenzene (m-DIPB) from a mixture of m-DIPB and p-diisopropylbenzene (p-DIPB) which comprises distilling a mixture of m-DIPB and p-DIPB in a rectification column in the presence of an extractive agent, recovering the m-DIPB as overhead product and obtaining the p-DIPB and the extractive agent from the stillpot, wherein said extractive agent comprises tributyl phosphate.

* * * * *